United States Patent [19]

Wallace et al.

[11] Patent Number: 5,670,320
[45] Date of Patent: Sep. 23, 1997

[54] DETECTION OF MITOCHONDRIAL DNA MUTATION 14459 ASSOCIATED WITH DYSTONIA AND/OR LEBER'S HEREDITARY OPTIC NEUROPATHY

[75] Inventors: Douglas C. Wallace; Michael D. Brown, both of Atlanta, Ga.

[73] Assignee: Emory University, Atlanta, Ga.

[21] Appl. No.: 339,912

[22] Filed: Nov. 14, 1994

[51] Int. Cl.[6] .......................... C12Q 1/68; G01N 33/53; C12M 1/00; C07H 21/02
[52] U.S. Cl. ....................... 435/6; 435/71; 435/72; 435/291; 435/287; 536/24.3; 536/24.31; 536/24.32; 536/266
[58] Field of Search ..................... 435/6, 7.1, 7.21, 435/291, 287; 536/24.3, 24.31, 24.32, 26.6; 935/76, 77, 78

[56] References Cited

PUBLICATIONS

Jun et al. "A mitochondrial DNA mutation at nucleotide pair 14459 of the NADH dehydrogenase subunit 6 gene associated with maternally inherited Leber hereditary optic neuropathy and dystonia" Proc. Natl. Acad. Sci. USA vol. 91, pp. 6206–6210, 1994.

Novotny, et al., "Leber's disease and dystonia: A mitochondrial disease," *Neurology* 36(8):1053–1060 (Aug., 1986).

Wallace, Douglas C., "Diseases of the Mitochondrial DNA," *Annu. Rev. Biochem.* 1992 61:1175–1212 (1992).

Shoffner, et al., "Subacute necrotizing encepalopathy: Oxidative phosphorylation defects and the ATPase 6 point mutation," *Neurology* 42(11):2168–2174 (Nov., 1992).

Johns, et al., "Leber's Hereditary Optic Neuropathy," *Arch. Ophthalmol.* 111:495–498 (Apr., 1993).

Brown, et al., "Mitochondrial DNA Complex I and III Mutations Associated with Leber's Hereditary Optic Neuropathy," *Genetics* 130:163–173 (Jan., 1992).

Brown, et al., "Leber's hereditary optic neuropathy: a model for mitochondrial neurodegenerative diseases," *FASEB J.* 6:2791–2799 (Jul., 1992).

*Primary Examiner*—Ardin H. Marschel
*Assistant Examiner*—Jezia Riley
*Attorney, Agent, or Firm*—Needle & Rosenberg, P.C.

[57] ABSTRACT

The present invention provides an assay for diagnosing or predicting a predisposition to dystonia and/or Leber's Hereditary Optic Neuropathy by detecting the presence of a mutation in mitochondrial DNA, in the oxidative phosphorylation (OXPHOS) gene ND6, that causes a substitution in amino acid 72 of the ND6 polypeptide. In particular, the mutation can be at mtDNA position 14459. Also provided are therapeutic treatments for dystonia and/or Leber's Hereditary Optic Neuropathy, as well as methods of screening compounds for effectiveness in treating these diseases and an animal model.

5 Claims, 1 Drawing Sheet

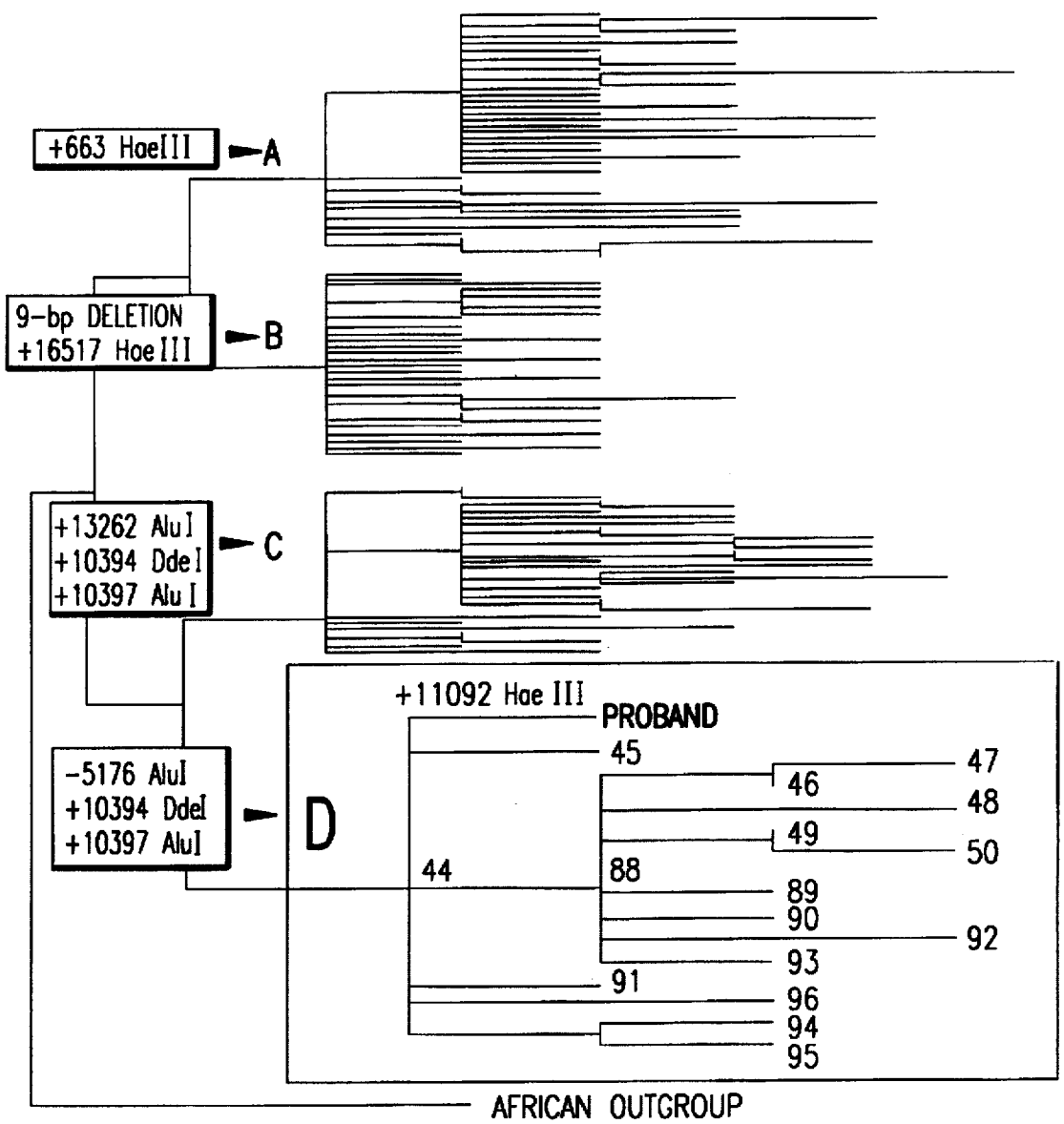

SEQUENCE LISTING ( 1 ) GENERAL INFORMATION:

( i i i ) NUMBER OF SEQUENCES: 7

( 2 ) INFORMATION FOR SEQ ID NO:1:

```
        ( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: other nucleic acid ( x i ) SEQUENCE DESCRIPTION: SEQ ID NO:1:
```

TAGCCATCAC TGTAGTATAT                                                                                             20

( 2 ) INFORMATION FOR SEQ ID NO:2:

```
        ( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: other nucleic acid ( x i ) SEQUENCE DESCRIPTION: SEQ ID NO:2:
```

ATATACTACA GCGATGGCTA                                                                                             20

( 2 ) INFORMATION FOR SEQ ID NO:3:

```
        ( i ) SEQUENCE CHARACTERISTICS:
                ( A ) LENGTH: 29 base pairs
                ( B ) TYPE: nucleic acid
                ( C ) STRANDEDNESS: single
                ( D ) TOPOLOGY: linear ( i i ) MOLECULE TYPE: other nucleic acid ( x i ) SEQUENCE DESCRIPTION: SEQ ID NO:3:
```

ATGCCTCAGG ATACTCCTCA ATAGCCATC                                                                                   29

( 2 ) INFORMATION FOR SEQ ID NO:4:

```
        ( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: other nucleic acid ( x i ) SEQUENCE DESCRIPTION: SEQ ID NO:4:
```

AGGATCAGGC AGGCGCCAAG                                                                                             20

( 2 ) INFORMATION FOR SEQ ID NO:5:

```
        ( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: other nucleic acid ( x i ) SEQUENCE DESCRIPTION: SEQ ID NO:5:
```

ATGCCTCAGG ATACTCCTCC AATAGCCGTC                                                                                  30

( 2 ) INFORMATION FOR SEQ ID NO:6:

```
        ( i ) SEQUENCE CHARACTERISTICS:
                ( A ) LENGTH: 20 base pairs
                ( B ) TYPE: nucleic acid
                ( C ) STRANDEDNESS: single
```

-continued (D) TOPOLOGY: linear (ii) MOLECULE TYPE: other nucleic acid (xi) SEQUENCE DESCRIPTION: SEQ ID NO:6:

ATACTCCTCA ATAGCCATCA 20

(2) INFORMATION FOR SEQ ID NO:7:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:7:

CCTCAATAGC CATCACTGTA GT 22

DETECTION OF MITOCHONDRIAL DNA MUTATION 14459 ASSOCIATED WITH DYSTONIA AND/OR LEBER'S HEREDITARY OPTIC NEUROPATHY

The invention described herein was made with Government support under grant nos. NS21328 and GM 46915 awarded by the National Institutes of Health and by a Muscular Dystrophy Foundation clinical investigation grant. The Government has certain rights in this invention.

BACKGROUND OF THE INVENTION

1. Field of the Invention

The present invention relates to a method of detecting neuromuscular disease in a patient, particularly dystonia and/or Leber's hereditary optic neuropathy. More particularly, the invention relates to detecting a point mutation at the mitochondrial DNA nucleotide position 14459 in the patient's DNA that detects the presence of dystonia and/or Leber's hereditary optic neuropathy.

2. Background Art

Leber's hereditary optic neuropathy (LHON) is associated with a rapid bilateral loss of central vision caused by neuroretinal degeneration. The median age at the onset of vision loss is 20 to 24 years, but ranges from adolescence to late adulthood. In numerous large pedigrees, LHON patients have been found to be related exclusively through the maternal lineage.

Human mitochondrial DNA (mtDNA) is maternally inherited. Each cell contains thousands of copies of mtDNA in the matrixes of the mitochondria. Each mtDNA codes for a large and a small ribosomal RNA, 22 transfer RNA's, and 13 polypeptides that function in the enzyme complexes of oxidative phosphorylation.

The mitochondria of eukaryotic cells generate adenosine triphosphate (ATP) via oxidative phosphorylation (OXPHOS), an enzyme pathway consisting of five multi-subunit enzyme complexes located within the mitochondrial inner membrane. This pathway is subdivided into the electron transport chain (complexes I to IV) and the ATP synthase (complex V). Complexes I, III, IV, and V are assembled from both nuclear DNA and mtDNA gene products. The mtDNA contributes seven polypeptide subunits (ND1, 2, 3, 4, 4L, 5, 6) to complex I (NADH:ubiquinone oxidoreductase, EC 1.6.5.3); one subunit (cytochrome b) to complex III (ubiquinol:cytochrome c oxidoreductase, EC 1.10.2.2); three subunits (CO I, II, III) to complex IV (cytochrome c oxidase, EC 1.9.3.1); and two subunits (ATPase 6, 8) to complex V (ATP Synthase, EC 3.6.1.34). The mtDNA also encodes the 12S and 16S rRNAs and the 22 tRNAs required for mitochondrial protein synthesis.

A broad spectrum of neuromuscular diseases has recently been associated with alterations in mitochondrial structure and in the capacity to generate ATP. Some of these "mitochondrial encephalomyopathies," such as LHON, primarily affect the central nervous system, but others, such as myoclonus epilepsy and ragged red fiber disease (MERRF) or mitochondrial encephalomyopathy lacticacidoses and stroke-like symptoms (MELAS), affect the skeletal muscle, heart, kidney, and liver as well. Dystonia patients can exhibit unilateral or bilateral basal ganglia lesions and may also exhibit complex neurological degeneration that includes dystonia (general and segmental), pseudobulbar signs, corticospinal tract dysfunction, optic nerve atrophy and mental retardation. Some forms of dystonia associated with basal ganglia degeneration include Hallervorden-Spatz disease, striatal syndrome and infantile bilateral striatal necrosis.

LHON is a midlife disease associated with acute or subacute central vision loss and has been shown to result from missense mutations in the mtDNA genes encoding subunits of OXPHOS complexes I, III, or IV. The most common LHON mutations occur in complex I genes and include a G to A transition at nucleotide pair (np) 3460 in ND1; a G to A transition at np 11778 in ND4 (U.S. Pat. No. 5,185,244); and a T to C transition at np 14484 in ND6. Leigh's syndrome is a rapidly progressive, childhood neurodegenerative disease associated with symmetric basal ganglia lesions that has been shown to result in a number of cases from mutations at np 8993 within the mitochondrial ATPase 6 gene. Thus, mtDNA missense mutations in complex I and V genes can yield clinical phenotypes similar to those seen in LHON and dystonia.

Moreover, patients with idiopathic dystonia have been shown to have significant respiratory complex I defects when assayed from blood platelets, and chronic treatment of mammals with the complex IV inhibitor sodium azide or the complex II inhibitor 3-nitropropanoic acid produce basal ganglia lesions in primates and rodents similar to those seen on CT and MRI analysis of severely affected LHON and dystonia patients.

Thus, various neuromuscular diseases are associated with several genetic mutations, many of which, by virtue of being mutations in mitochondrial DNA, are maternally transmitted.

Therefore, there is a strong need for means to identify the cause of such diseases, so that therapies can be instituted prior to onset of symptoms, and so that family planning issues can be addressed. Accurate determination of the specific cause of the disease in a subject will allow more precise treatment. The present invention provides the discovery of a pathogenic mitochondrial mutation in the OXPHOS gene ND6 at position 14459 (MTND6*LDYT14459A), which is associated with LHON and/or dystonia. This mutation has been found in several independent pedigrees, all with similar clinical manifestations. Thus the present invention provides a predictive and/or diagnostic assay for LHON and dystonia, as well as therapeutic treatments and models for screening drugs for usefulness in treatment of LHON and/or dystonia.

SUMMARY OF THE INVENTION

The present invention provides a method for detecting in a subject the presence of dystonia and/or LHON and associated neuromuscular diseases by testing the mtDNA in any cell from the subject for the presence of a point mutation at the mitochondrial (mtDNA) nucleotide pair (np) 14459 of the mitochondrial genome or for the presence of mutation that substitutes the alanine at amino acid 72 for another amino acid. The mutation is heteroplasmic in some maternal relatives of afflicted subjects, and changes a moderately conserved alanine amino acid at amino acid 72 in the most conserved region of the ND6 polypeptide.

Accordingly, one of the objectives of this invention is to provide a method of detecting neuromuscular disease, particularly LHON and/or dystonia, in a patient by detecting the presence of this mutation. A further object of this invention is to provide a method to test any cell of a patient for the presence of a point mutation at np 14459 in the patient's mtDNA or a mitochondrial mutation that causes a substitution of the alanine residue at amino acid 72 of the ND6 polypeptide.

This invention also provides a method of detecting in a subject a predisposition to optic nerve atrophy or basal ganglia degeneration associated with the presence of a point mutation at position 14459 of mitochondrial DNA, comprising detecting in a sample from the subject the presence of a mutation at position 14459 of mitochondrial DNA, the presence of the mutation indicating the predisposition to optic nerve atrophy or basal ganglia degeneration in the subject.

The present invention further provides a method of predicting a predisposition to developing a class of dystonia and/or LHON, comprising detecting in a sample from a subject the presence of a mutation at position 14459 of mitochondrial DNA, the presence of the mutation indicating a predisposition to developing the class of dystonia and/or LHON in the subject.

The present invention further provides a method of screening a compound for treating dystonia and/or LHON comprising administering the compound to an animal having a nucleic acid encoding a mutant mitochondrial ND6 polypeptide having an amino acid other than alanine at amino acid 72 and monitoring the effect of the compound on dystonia and/or LHON in the animal.

The present invention further provides an isolated nucleic acid encoding a mutant mitochondrial ND6 polypeptide having an amino acid other than alanine, such as valine, at amino acid 72. Thus, for example, the present invention provides an isolated nucleic acid encoding a mutant mitochondrial ND6 polypeptide, wherein the nucleic acid has a mutation at nucleotide position 14459 of the mitochondrial DNA.

Accordingly, it is an object of the present invention to provide nucleic acids capable of detecting the presence of the np 14459 mutation in a subject as well as nucleic acids useful for treating subjects having the mutation. It is also an object of the instant invention to provide, e.g., antibodies capable of detecting the presence of the mutant protein ND6 (having a substitution at amino acid 72). Such methods allow early prediction of a predisposition to and/or diagnosis of the clinical manifestations of the presence of such a mutation in ND6, e.g., LHON and/or dystonia.

Thus, the instant invention provides an isolated nucleic acid fragment, or related coding macromolecule, such as a protein nucleic acid (PNA), of at least 8 nucleotides in length that specifically hybridizes with the mutant nucleic acid. Such fragments provide detection of the presence of the mutant nucleic acid as well as therapeutic treatments to block the expression of the mutant protein. Thus, the present invention provides a method of treating a subject having a class of dystonia and/or Leber's Hereditary Optic Neuropathy comprising administering to the subject an oligonucleotide of at least 8 nucleotides in length that specifically hybridizes to a region of ND6 RNA encompassing the region encoding valine at amino acid 72 of ND6.

The present invention additionally provides a transgenic, non-human animal having a nucleic acid encoding a mutant mitochondrial ND6 polypeptide having an amino acid other than alanine at amino acid 72.

Accordingly, the present invention also provides a method of screening a compound for effectiveness in reducing or eliminating a clinical manifestation of dystonia and/or Leber's Hereditary Optic Neuropathy, i.e., for treating dystonia and/or LHON, comprising administering the compound to an animal having a nucleic acid encoding a mutant mitochondrial ND6 polypeptide having an amino acid other than alanine at amino acid 72, and determining the effect of the compound on the clinical manifestation, thereby screening the compound for effectiveness in reducing or eliminating the clinical manifestation of dystonia and/or LHON.

BRIEF DESCRIPTION OF THE DRAWINGS

FIG. 1 shows Native American mtDNA phylogenetic tree including the LHON and dystonia haplotype. The Native American controls represent 508 individuals and 120 distinct haplotypes. The haplogroup D samples represent 59 individuals and 16 distinct haplotypes. A HaeIII site loss at np 11092 results in a novel LHON and dystonia haplotype.

DETAILED DESCRIPTION OF THE INVENTION

The present invention may be understood more readily by reference to the following detailed description of specific embodiments and the Examples included therein.

A novel point mutation in the ND6 subunit of Complex I at position 14459 of the mitochondrial DNA (mtDNA) (MTND6*LDYT14459A) is herein identified as a mutation for the highly tissue specific disease, Leber's hereditary optic neuropathy (LHON) and/or dystonia. In the example, a moderately conserved alanine is changed by the mutation to a valine at amino acid 72 of the ND6 polypeptide, which is thought to be located in an iron-sulfur center of Complex I (Wallace, D. C., Annu. Rev. Biochem. 61:1175–1212 (1992)).

Affected pedigree members of affected individuals display significant variability in the severity of disease expression. Individuals with the mildest manifestations have adolescent onset LHON. Severely affected individuals experience the childhood onset of a severe, generalized dystonia which can be associated with variable degrees of dementia, bulbar dysfunction, corticospinal tract dysfunction, and short stature. Brain imaging can reveal bilateral and symmetrical basal ganglia abnormalities that are similar to those observed in Leigh's disease.

As the first genetic abnormality that has been identified to cause generalized dystonia, the presence of this mutation demonstrates that nuclear DNA or mtDNA mutations in oxidative phosphorylation genes are important considerations in the pathogenesis of dystonia.

The present invention relates to the discovery of a class of dystonia and/or Leber's Hereditary Optic Neuropathy (LHON) characterized by the presence of a mutation at position 14459 of human mitochondrial DNA, which is in the ND6 gene (MTND6). The mutation alters amino acid 72 in the NADH dehydrogenase subunit 6 (ND6) polypeptide from its normal alanine. The nucleotide sequence of the ND6 gene is known (Anderson, S., et al., Nature 290:457–465 (1981). Therefore, as used in the claims, "a class of dystonia and/or Leber's Hereditary Optic Neuropathy" refers to those cases of dystonia and/or LHON characterized by the presence of any mutation that alters amino acid 72 of ND6 (also termed MTND6) from the normal alanine. Other mitochondrial or nuclear DNA mutations can additionally be present in the subject. A mutation encompassed by this class can include mutations that correlate to nucleotide pair (np) 14459 and/or 14460 in the human mitochondrial genome, as long as the mutation encodes an amino acid other than alanine at amino acid 72 of the ND6 polypeptide. For example, at np 14459, the normal guanine (G) residue can be, e.g., adenine (A). Included in this class are subjects which are heteroplasmic or homoplasmic for the mutation.

The presence of this class of dystonia and/or LHON can therefore be detected in a subject by detecting in a sample from the subject the presence of a mutation in the subject's mitochondrial DNA that causes the mtDNA to encode, in the ND6 polypeptide, an amino acid other than the normal, wild-type alanine, e.g., a mutation at the position corresponding to np 14459 of human mitochondrial DNA. For example, a G-to-A transition at np 14459 changes the alanine residue at residue 72 of ND6 to valine.

As used herein, "predicting a predisposition to developing a class of dystonia and/or Leber's Hereditary Optic Neuropathy" means determining an increased probability of developing dystonia and/or LHON during the subject's lifetime. Depending on the percentage of mutant mitochondrial DNAs, it is possible to predict the likelihood of an individual developing disease. For example, the higher the percentage of mutant mtNAs, the lower the OXPHOS complex I would be, thus increasing the probability of LHON and/or dystonia By the "presence" of a mutation in mitochondrial DNA is included than an affected individual can be heteroplasmic (i.e., have both normal and mutant mtDNA) for the mutated DNA, and therefore, it is included that there may additionally be the presence of some normal mitochondrial DNA in a sample in which mutated NDA is present.

As used herein, "diagnosing" means using the presence of a mutation at np 14459 of mitochondrial DNA as a factor in making dystonia and/or LHON diagnosis. The detection of the mutation can be a step in the disease state diagnosis.

"Selectively hybridizing" as used herein means the formation of hybrids between a selected nucleic acid fragment (e.g., a nucleic acid which may include substitutions, deletions, and/or additions, such as a primer probe or other oligonucleotide) and a specific target nucleic acid (e.g., a nucleic acid having the mutated sequence), wherein the probe preferentially hybridizes to the specific target such that, for example, a band corresponding to the mutated DNA or restriction fragment thereof can be identified on a Southern blot, whereas a corresponding normal or wild-type DNA is not identified or can be discriminated from a variant DNA on the basis of signal intensity. Hybridization probes capable of selective hybridization to detect a single-base mismatch may be designed according to methods known in the art. In particular, selective hybridization with the mtDNA having the mutation at np 14459 means hybridization conditions that allow hybridization, at the region of np 14459, to the mtDNA having the mutation at np 14459 but not to the wild-type np 14459 mtDNA. These selective conditions can be readily determined by hybridization of the specific probe to controls, a known mutant and a known wild-type sample. Relatedly, specific hybridization means that the hybrid forms in the virtual absence of non-specific binding.

As used herein, "selectively amplifying" mitochondrial DNA having the mutation at position np 14459 means amplifying only mitochondrial DNA having the specific mutation and amplifying normal wild-type DNA either very minimally or, preferably, only specific for the mutated DNA. Conditions for amplification must be such that amplification of mutant DNA can be distinguished from background, minimal amplification, such as of wild-type DNA. Such conditions can readily be determined utilizing control reactions having a mutant and a wild-type sample. Conditions of amplification can be varied to achieve the proper stringency according to known parameters in the art.

As used herein, "isolated" or "purified" means substantially free of the contaminants associated with the nucleic acid, polypeptide, or antibody occurring in a natural environment.

In particular, the present invention provides an isolated double-stranded nucleic acid functionally encoding a mutant mitochondrial ND6 polypeptide having an amino acid other than alanine at amino acid 72. The nucleic acid contains sequences, as known in the art, to allow expression of the encoded polypeptide. The ND6-encoding sequence can be the human sequence or an animal sequence, such as the mouse ND6 homolog, for use in creating a transgenic animal, e.g., a transgenic mouse. The coding sequence can be cloned, in pans or as a whole, in a suitable cloning vector and a suitable expression vector.

As used herein, "nucleic acid fragment" refers to a nucleic acid which corresponds to the mutant ND6 sequence and has sufficient nucleotides surrounding the codon at the mutation position(s) to distinguish the nucleic acid from nucleic acids encoding non-related genes. Nucleic acid homology software is well-known in the art for searching sequences in databanks, thereby readily identifying whether a portion of a nucleic acid containing the mutation that does not occur in other known nucleic acids, and therefore whether it falls within the term "nucleic acid fragment" as used herein. For example, DNASIS (Hitachi Software Engineering Co., Ltd.) can be used to search both the GENBANK and EMBL databases for complementarity to any selected nucleic acid fragment.

The specific length of the nucleic acid is a matter of routine choice based on the desired function of the sequence. For example, if one is making probes to detect the presence of the mutation in position np 14459 in a sample, the length of the nucleic acid is preferably small, but must be long enough to prevent hybridization to undesired background sequences. However, if the desired hybridization is to a nucleic acid which has been amplified, background hybridization is less of a concern and a smaller probe can be used. In general, such a probe will be between 10 and 100 nucleotides, especially between 10 and 40 and preferably between 15 and 25 nucleotides in length. For uses of these fragments as primers, generally the length can be any of a number of sizes, such as about 8 nucleotides to about 30 nucleotides, with a preferred size of about 9 to about 11 nucleotides. It is apparent that species variation within the sequence, especially at the wobble position, can be incorporated into the polynucleotides of the invention.

Nucleic acids can also include oligonucleotides that can be transferred into affected cells to reduce or eliminate the clinical effects of the mutation. The nucleic acids can be single- or double-stranded. Nucleic acid fragments can range in size, and will generally be around 10 to 40 nucleotides in length, and preferably around 20–25 nucleotides. These fragments can comprise antisense nucleic acids which can bind specifically to the mutated mtDNA, in the region including np 14459, to block expression of the mutant polypeptide, but not the wild-type. Fragments having this selectivity can readily be determined, as described herein and known in the art. These oligonucleotides can be RNA, DNA or "protein nucleic acids" (nucleic acids having a backbone made of protein rather than sugar-phosphate). These oligonucleotides can be circularized prior to transference to render them more resistant to degradation in the cell.

The nucleic acids described herein can be transferred into a cell that did not previously contain the specific nucleic acid. Transference can be done by any of several standard methods, such as electroporation, calcium chloride precipitation, microinjection, and liposome-mediated transfection. The cell can be one capable of expressing the nucleic acid, i.e., transcribing and translating the specific nucleic acid transferred into it. The cell can be prokaryotic, such as an *E. coli* derivative, which can be useful for producing quantities of the ND6 polypeptide encoded by the transferred nucleic acid, or the cell can be eukaryotic, such as a mammalian, e.g., mouse, cell useful for creating transgenic animals. The DNA sequences functionally encoding a polypeptide or antisense RNA can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362). The protein expressed by these cells can be harvested from the cell and purified to the desired extent by standard purification procedures.

Polynucleotides encoding a mutant or wild-type ND6 polypeptide may include sequences that facilitate transcription (expression sequences) and translation of the coding sequences such that the encoded polypeptide product is produced. Construction of such polynucleotides is well-known in the art and is described further in Maniatis et al., *Molecular Cloning: A Laboratory Manual*, 2nd Ed., Cold Spring Harbor Laboratory, Cold Spring Harbor, N.Y. (1989). For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. Such control sequences can be the native ND6 control sequences or sequences exogenous to the ND6 gene.

Complementary antisense polynucleotides can include soluble antisense RNA or DNA oligonucleotides which can hybridize specifically to a mutant MTND6 and prevent transcription of the mutant mRNA and/or translation of the encoded polypeptide (Ching et al., *Proc. Nat'l Acad Sci.* (U.S.A.) 86:10006–10010 (1989); Broder et al., *Ann. Int. Med.* 113:604–618 (1990); Loreau et al. *FEBS Letters* 274:53–56 (1990); Holcenberg et al., WO91/11535; U.S. Ser. No. 07/530,165 ("new human CRIPTO gene"); WO91/09865; WO91/04753; WO90/13641; and EP 386563). The antisense polynucleotides therefore inhibit production of the mutant ND6 polynucleotides. Antisense polynucleotides may preferentially inhibit transcription and/or translation of mRNA corresponding to mutant (or wild-type) polypeptides.

Antisense polynucleotides may be produced from a heterologous expression cassette in a transfectant cell or transgenic cell or animal, preferably where the expression cassette contains a sequence that promotes cell-type specific expression Wirak et al., *EMBO* 10:289 (1991)). Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, D. A. Melton, Ed., Cold Spring Harbor Laboratory, Cold Spring Harbor, N.Y. (1988).

As used herein, the term "mutant" or "mutation" refers to a mutation in the mtDNA that alters the amino acid encoded at amino acid 72 of the ND6 mitochondrial gene. "Mutant" also can specifically refer to a mutation at position np 14459. It can particularly refer to a G-to-A transition at np 14459. It can also include other mutations wherein a codon is changed from specifying alanine at amino acid 72 to another amino acid. Thus, other mutations which cause a change in the codon from alanine can be associated with dystonia and/or LHON, with optic nerve atrophy and/or with basal ganglia degeneration, especially where the change is to valine, are included herein.

An antibody capable of selectively binding to the mutant ND6 protein having an amino acid other than alanine, e.g. valine, at amino acid 72 can readily be generated according to standard procedures and purified. By "capable of selectively binding" is meant that the antibody can hybridize preferentially to a mutant ND6 polypeptide rather than the wild-type (for amino acid 72) ND6 polypeptide and can therefore be utilized to distinguish between the mutant and the wild-type polypeptide. An antibody can include antibody fragments such as Fab fragments which retain the binding activity. Antibodies can be made as described in, e.g., Harlow and Lane, *Antibodies: A Laboratory Manual*, Cold Spring Harbor Laboratory, Cold Spring Harbork, N.Y. (1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen DNA clone libraries for cells secreting the antigen. Those positive clones can then be sequenced as described in the Examples or by other methods (see, for example, Kelly et al., *Bio/Technology* 10:169–175, 1992).

The term "compound" is used herein to denote a chemical compound, a mixture of chemical compounds, a biological macromolecule, or an extract made from biological materials such as bacteria, plants, fungi, or animal (particularly mammalian) cells or tissues. For example, the compound can be a nucleic acid or a polypeptide. Compounds are evaluated for potential biological activity in reducing or eliminating a clinical manifestation of dystonia and/or LHON by inclusion in screening assays. The effect of the compound on dystonia and/or LHON can then be monitored to determine any reduction or elimination of a clinical manifestation of dystonia and/or LHON.

By "treating" dystonia and/or LHON is meant reducing or preventing any of the clinical manifestations of dystonia and/or LHON. These manifestations are known in the art and include general or segmental dystonia, pseudobulbar signs, unilateral or bilateral basal ganglia lesions, corticospinal tract dysfunction, optic nerve atrophy and mental retardation. Signs of optic nerve atrophy can include retinal disk swelling, torturous vessels, and microangiopathy with telangiectasias.

A subject having the class of dystonia and/or LHON characterized by the presence of a mutation altering amino acid 72 of the MTND6 gene can be treated by administering to the subject a compound found by the present screening assay to reduce or eliminate a clinical manifestation of dystonia and/or LHON. Alternatively or in conjunction, a subject having this class of dystonia and/or LHON can be treated by administering to the subject an oligonucleotide that specifically hybridizes to a region of mutant ND6 RNA encompassing the region encoding valine at amino acid 72 of the DN6 polypeptide to prevent production of the mutant polypeptide. Such oligonucleotide preferentially binds to the mutant ND6 RNA present in the subject rather than the normal, wild-type ND6 RNA. The specific ND6 RNA encoded by the ND6 mtDNA of any given subject can be determined by standard methods, such as selective amplification or selective hybridization, as known in the art and described herein. An example of such an antisense oligonucleotide capable of specifically hybridizing to a G-to-A transition at np 14459 is listed herein as SEQ ID NO: 7 (nt 14445–14466). Another example is listed in SEQ ID NO: 1.

By "monitoring the effect" of a compound on dystonia and/or LHON is meant detecting and/or, when possible, measuring any change in a clinical manifestation of dystonia and/or LHON by the appropriate means for detecting such change, many of which are known in the art.

The detection of a mitochondrial DNA mutation altering the ND6 polypeptide at residue 72 can be performed by any means capable of detecting the mutation. Many detection methods for this diagnostic/predictive detection from a sample from a subject are known and standard in the art, as exemplified below.

For example, a differential hybridization of oligonucleotides can be utilized for assaying whether a point mutation exists at a specific nucleotide of a patient's mtDNA. This method involves hybridizing a sample of the patient's mtDNA with either an oligonucleotide probe that is complementary to normal mtDNA or one that is complementary to mutant mtDNA in the region surrounding the nucleotide, e.g., np 14459. The patient's mtDNA sample can contain either complete or partial mtDNA and may be either raw, purified, or amplified mtDNA.

Oligonucleotide detection probes may be prepared, for example, synthetically or by nick translation. The probes may be suitably labeled using, for example, a radio label, enzyme label, fluorescent label, biotin-avidin label and the like for subsequent visualization, for example by Southern blot hybridization. In the Southern blot example, the labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography. The labeled probe is reacted with a DNA sample bound to, for example, nitrocellulose under conditions of sufficient stringency to distinguish hybridization of a fully complementary oligonucleotide from hybridization of an oligonucleotide having one nucleotide mismatched. The stringency conditions can also be altered based upon the exact nucleotide composition of the oligonucleotide and the position within the oligonucleotide of the mismatched nucleotide. Tetra-alkyl ammonium salts bind selectively to A–T base pairs, thus displacing the dissociation equilibrium and raising the melting temperature. At 3M Me 4NCl this is sufficient to shift the melting temperature to that of G–C pairs. This results in a marked sharpening of the melting profile. The stringency of hybridization is usually 5° C. below the Ti (the irreversible melting temperature of the hybrid formed between the probe and its target sequence) for the given chain length. For 20mers the recommended hybridization temperature is about 58° C. The washing temperatures are unique to the sequence under investigation and need to be optimized for each variant. Many substrates other than filters can readily be employed for binding DNA for subsequent detection, such as plastic, well plates and magnetic beads, as known in the art.

A LHON/dystonia-specific oligonucleotide useful as a probe can, for example, have an adenine (A) at the position corresponding to np 14459 of mitochondrial DNA, e.g., the oligonucleotide provided herein as SEQ ID NO: 1 (nt 14451–nt 14470) or its complement. The wild-type oligonucleotide can have a C (hybridizing on the opposite strand) at the position corresponding to np 14459, e.g., the oligonucleotide listed herein as SEQ ID NO: 2 (nt 14470–14451) (5'–3').

The probes are preferably designed on the DNA strand appropriate to eliminate promiscuous G–T hybridization by avoiding the use of G or T at the informative position. Enriched mtDNA samples from subjects can be spotted onto duplicate filters by the alkaline dot blot method disclosed in *Proc. Nat'l. Acad. Sci.* USA 85:1629 (1988). The duplicate filters can be prehybridized and hybridized, e.g., at 44° C., one with the dystonia and/or LHON probe and the other with the wild-type. To eliminate non-specific hybridization, the filter with the dystonia and/or LHON probe can be washed at 47°–49° C. and the filter with the wild-type can be washed at 49°–51° C. After autoradiography, the samples from the dystonia and/or LHON patients containing the mutant base at np 14459 are strongly reactive with the dystonia and/or LHON probe and non-reactive or only very faintly reactive with the wild-type probe. Conversely, the non-mutant mtDNA samples react strongly only with the wild-type probe and not with the mutant probe. The two duplicate filters from each test individual can show reciprocal hybridization.

Additionally, detection of the mutation can be achieved by amplifying a region of the mtDNA that includes np 14459. Following amplification, the presence of the mutation at np 14459 in the amplified product can then be detected.

For example, the polymerase chain reaction (PCR) is one technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence of the mutations, synthetic oligonucleotides can be prepared which are complementary to sequences which flank the DNA of interest. Each oligonucleotide is complementary to one of the two strands. The DNA can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. For example, a forward primer extending from np 14430 to np 14458 (SEQ ID NO: 3) and a reverse primer extending from np 14874 to np 14855 (SEQ ID NO: 4) can be utilized, which would result in a 444-bp amplified product. A polymerase chain reaction (PCR), e.g., can then be performed by standard procedures, such as about 35 cycles of denaturing (94° for 1 minute), a brief annealing period at the predicted specific hybridization temperature (e.g., 59°–60° C., 30 seconds), followed by a period of DNA extension (72° C., 30 seconds), to amplify the region of mtDNA.

The amplified product can then be analyzed to determine the presence of the mutation in the amplified product. Several means can be utilized for the detection of the mutation. For example, the resulting DNA can be directly sequenced. Alternatively, the differential hybridization described above can be performed with one probe specific for the wild-type/normal nucleotide sequence and another probe specific for the mutation at np 14459.

Alternatively, to detect the presence of a 14459 mutation, e.g., a mutation-specific primer mismatch PCR can be employed for the amplification reaction, which can then be followed by Mae III restriction endonuclease digestion to determine the presence of the mutation. As described in more detail below, this method utilizes a PCR reaction in which a forward primer that spans np 14456, but does not extend beyond np 14458, and that has a mismatched G at np 14456, is used to create a Mae III site in the amplified product in the presence of a G-to-A transition at np 14459 on the L strand (e.g., the oligonucleotide corresponding to np 14430 to np 14458 (5' to 3') with a mismatched G at np 14456) (SEQ ID NO: 5). The reverse primer in this reaction can be any standardly-derived primer, e.g., extending from np 14874 to np 14855 (5'-3') (SEQ ID NO: 4). These example primers yield a PCR product of 444 bp. These PCR reactions are done at temperatures that will allow annealing of the mismatched primer, as exemplified herein. In subjects having a G-to-A transition at np 14459, the PCR product produced by this primer mismatch PCR will have a Mae III restriction endonuclease site, whereas in wild-type subjects, no Mae III site is generated. Thus digestion of the PCR products with Mae III will yield two fragments if the np 14459 mutation is present and one fragment if the np 14459 mutation is not present. The presence of one or two fragments can be determined by standard means, such as by gel electrophoresis.

Furthermore, as an additional example, detection of the presence of a mutation in the amplified product can be accomplished by a selective, differential amplification method for assaying whether a point mutation exists at 14459 of a patient's mtDNA. This method involves analysis of the end products of a PCR that employs a sample of the patient's mtDNA and a pair of oligonucleotide primers, specific to either normal mtDNA or mutant mtDNA, constructed such that the 3' end of one primer is located at np 14459. The patient's mtDNA sample can contain either complete or partial mtDNA and may be either raw, purified, or amplified mtDNA. The primers that are complementary to normal mtDNA allow amplification of a patient's mtDNA only if that mtDNA does not possess the np 14459 mutation. Conversely, primers that are complementary to mutant mtDNA allow amplification only if the patient's mtDNA possesses the point mutation. Thus, analysis of the end products of a PCR using either set of primers determines whether the point mutation is present in the patient's mtDNA. For example, a mutation-specific primer having a mutant nucleotide at np 14459 in dystonia and/or LHON patients, such as that listed as SEQ ID NO: 6 (np 14440–14459) can be utilized in a PCR reaction with a primer that hybridizes to a non-mutated region (e.g., the oligonucleotide listed as SEQ ID NO: 4), which would result in a 434 bp product.

Thus, in a mutant-specific reaction, only the sample having the mutant mtDNA will produce an amplification product. If an amplified product is detected in such a reaction, therefore, the presence of the mutation in the sample is thereby detected. Detection of the amplified product can be by any of several standard methods, such as electrophoresis on an agarose or polyacrylamide gel and ethidium bromide staining to visualize the nucleic acids on the gel.

PCR conditions for selective PCR must be such that a mismatched primer cannot anneal. Particularly, the annealing step must be brief enough and at a high enough temperature to guarantee only the exact DNA match will anneal and be elongated in the polymerization. Exact conditions can be readily determined based upon the melting temperature (Tm) of the oligonucleotides, as is standard in the art. For example, for the primer pair exemplified by SEQ ID NOS: 4 and 6, the following PCR can be performed: 35 cycles of denaturing (94° C. for 1 minute), brief annealing (59°–60° C. for 30 seconds), and extension (72° C. for 30 seconds) in standard reaction buffers.

Alternatively, an adaptation of PCR called amplification of specific alleles (PASA) can be employed; this uses differential amplification for rapid and reliable distinction between alleles that differ at a single base pair. Other techniques, such as 3SR, which utilize RNA polymerase to achieve high copy number, can also be used where appropriate.

Selective detection can also be done, for example, by ligase chain reaction (LCR). LCR involves the use of mismatch oglionucleotides which are fully complementary with the target sequence except at the point of the mutation. The target sequence is allowed to hybridize with two adjacent oligonucleotides. The nucleotide at the adjoining ends is chosen corresponding to the mutant nucleotide. When the oligonucleotides correspond to the base at the mutant site, then the ligase will link the two oligonucleotides together. When the alternate base is present, then the oligonucleotides remain separate. Thus, the presence or absence of the mutant base can be detected by the linkage or lack thereof of the tester oligonucleotides.

For example, a first oligonucleotide having a 3' hydroxyl adjacent to the mutant nucleotide, e.g., corresponding to nt 14450–14458, can be used in both the normal-specific reaction and the mutant-specific reaction. A second oligonucleotide is utilized as a primer that has its 5' phosphate end at the 14459 nucleotide, e.g., corresponding to nt 14459–14470. The second nucleotide is generated to be specific for the mutant ND6 gene by virtue of the nucleotide chosen for the oligonucleotide corresponding to nt 14459. If an LCR product is detected, then the mutant mt DNA is present. The LCR products can be detected, e.g., by utilizing a detectable label on the second mutation-specific oligonucleotide.

In general, primers for PCR and LCR are usually about 20 bp in length and the preferable range is from 15–25 bp. For PCR, better amplification is generally obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on genetic material (DNA or RNA) obtained from an individual, it can serve as a method of detecting the presence of the mutations.

Mitochondrial DNA is derived from any cell from the patient by various methods (see, e.g., U.S. Pat. No. 5,185, 244). For instance, hair follicles can be placed in distilled water and heated to boiling to release the mtDNA; alternatively, the hair follicles can be placed in a 0.9% NaCl phosphate buffered solution and heated to boiling to release the mtDNA.

As another example, blood can be fractionated on Ficoll-Hypaque gradients (Pharmacia, Piscataway, N.J.) followed by transforming the lymphocytes with Epstein-Barr virus as disclosed in *Am. J. Hum. Genet.* 38:461 (1986). Purified mtDNA can be obtained from these cells by enriching whole-cell lysates through precipitation of the chromatin with 1M NaCl. The mtDNA-rich supernatant can be further purified by proteinase digestion and organic extraction as disclosed in *Somat. Cell Mol. Genet.* 12:41 (1986). Alternatively, mtDNAs can be purified from isolated mitochondria by detergent lysis and separation with the use of two density-gradient centrifugations with a cesium-chloride-ethidium bromide solution.

A transgenic, non-human animal can be created as a model for dystonia and/or LHON. The animal can have a mutated ND6 gene which codes for an amino acid other than alanine at amino acid 72.

Transgenic, non-human animal models can be created for dystonia and/or LHON caused by the ND6 codon 72 mutation. The mutated ND6 gene can be introduced into the animal, and development of the clinical phenotype examined with and without metabolic or genetic therapy. Two approaches that can be utilized for introducing the ND6 codon 72 mutation into a laboratory animal, such as the mouse, are as follows. The first approach can be to generate a mouse cell line harboring a mutant mtDNA codon 72. This cell Free could be generated by either recovering the mutant mtDNA from an aged animal (mouse) or by introducing a mutated mtDNA through DNA transformation. Old animals accumulate a wide spectrum of deleterious somatic mutations. These can be rescued by fusing cytoplasmic fragments from post-mutation tissue with mtDNA-deficient cultured cells. The resulting cybrids (Bunn et al., *Proc. Natl. Acad. Sci.* (USA) 71:1681–1685 (1974); Wallace et al., *J. Cell Biol.* 67:174–188 (1975)) can then be used to transfer the mutations to female embryonic stem (ES) cells. These ES cells can then be introduced into mouse blastocysts and the resulting female chimeric mice bred for those which transmit the mutations (Frohman and Martin, *Cell* 56:145 (1985)). Alternatively, exogenous mtDNA carrying the mutant ND6 gene could be targeted to the mitochondria, thus introducing the mutant gene. The mutant mtDNA can then be transferred to embryonic stem cells from the transformed cell.

An alternative approach can be to introduce a mutant ND6 gene into the nucleus in cells of an animal model and have the mutant protein redirected to the mitochondria. The animal (mouse) gene can be cloned, and the mtDNA genetic code modified to equal the nuclear DNA code. The ND6 codon 72 can also be mutated to the pathogenic amino acid. The ND6 gene can then be fused to an N-terminal mitochondrial targeting sequence, such as that from the ATP synthase β subunit, and the fusion gene placed under the control of a strong promoter such as methalothionine or α-actin gene promoters. The plasmid containing the construct can then be microinjected into fertilized oocytes, and the transgenic animals identified and bred. Animals harboring the mutant ND6 transgene under control of the metallothionine promoter can be fed zinc to increase the ND6 expression and modulate the severity of the disease (Gordon, 1994, Production of Transgenic Mice. In *Guide to Techniques in Mouse Development*, Wassarman, P. M., DePamphilis, M. L. eds. San Diego, Academic Press, 747–771, and Hogan, B. L. M. H. et al., 1986, *Manipulating the Mouse Embryo*, Cold Spring Marbor Laboratory Press).

An animal having a transferred, exogenously derived ND6 gene, such that an DN6 polypeptide having an amino acid other than alanine at amino acid 72 is present in the animal, can be utilized to screen compounds for reducing or preventing a clinical manifestation of dystonia and/or LHON. The animal can have more mutations than the np 14459 mutation. Screening is performed by administering the compound to the animal and determining the effect of the compound on the clinical manifestation. A compound reducing or eliminating a clinical manifestation is then a candidate for treating dystonia and/or LHON, i.e., for reducing or eliminating a clinical manifestation of dystonia and/or LHON in a subject.

Knowledge of the presence of the ND6 np 14459 mutation in codon 72 offers gene therapy protocols for this form of dystonia and/or LHON. A variety of somatic and germline gene therapies can be utilized. Somatic gene therapy can permit treating the symptoms of the affected patient; whole germline therapy can permit treating of offspring. Two major approaches can be utilized for somatic gene therapy. The first involves fusing cytoplasm fragments derived from cells of normal individuals to the cells or tissues of the patient. This can deliver more normal mtDNAs to the tissue, reducing the biochemical defect and diminishing the symptoms. A preferable tissue can be the brain. A second somatic approach can be to clone the normal ND6 gene, alter the mtDNA genetic code to the universal code, add a mitochondrial targeting peptide to the amino terminal end of the protein, and place the gene under the control of a nuclear promoter (e.g. metallothionine or α-actin). This construct can then be transformed into the cells or tissues of the patient, where it can integrate and be expressed in the nucleus. The protein can then be directed to the mitochondria by the targeting peptide where it can be processed, leading to incorporation of the normal ND6 polypeptide into complex I. For example, skin fibroblast cells can be constructed as described above to contain the normal ND6 gene and returned to, for example, the patient's brain.

Thus, a preferable nucleic acid for gene therapy can be a nucleic acid encoding a wild-type ND6 polypeptide having additional amino acids at the C-terminal end that encode a mitochondrial-targeting polypeptide. Standard cloning methods for generating such chimeric proteins can be utilized, and known mitochondria-targeting sequences can be encoded by the nucleic acid.

Germline gene therapy can also be useful for this mutation. For women harboring the mutant mtDNA, the oocytes could be collected and fertilized in vitro with their husband's sperm. After initial cleavage, the morula nuclei can be removed from the mutant cytoplasm and microinjected into an enucleated egg from a normal donor. The resulting embryo with normal mtDNAs can then be reimplanted into the mother.

Compounds can be administered to a subject or an animal model by any of many standard means for administering the particular compound. Additionally, particularly for the screening assays, compounds can be administered orally, parenterally (e.g., intravenously), by intramuscular injection, by intraperitoneal injection, topically, transdermally, or the like. Compounds can be administered, e.g., as a complex with cationic liposomes, or encapsulated in anionic liposomes. Compositions can include various amounts of the selected compound in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions.

Statement Concerning Utility

The present invention provides a method of detecting in a subject the presence of a class of dystonia and/or Leber's Hereditary Neuropathy. The invention also provides a means of predicting a predisposition to dystonia and/or Leber's Hereditary Neuropathy. This detection and prediction is done by detecting in a sample from a subject a mutation in their mitochondrial DNA that alters amino acid 72 in the ND6 gene. It therefore provides the capability of anticipating the onset of clinical manifestations of the disease prior to the onset of the disease. Therefore, treatments for delaying or preventing the manifestations of the disease can be instituted as early as possible. For example, preventative metabolic therapy to increase mitochondrial energy output can be instituted, and natural metabolites, such as coenzyme Q, that can bypass the block created by the mutant ND6, can be administered. Additionally, if the mutation is detected, gene therapy can be instituted to treat the disease. Both increasing the levels of the normal protein in cells in the body and decreasing the levels of the mutant protein in cells in the body can be beneficial in reducing or preventing clinical manifestations of the diseases.

Furthermore, family planning issues can be addressed based upon the knowledge gained from this invention. Onset of the disease can be in any range from early to mid-late onset, and predictability within families of inheritance of dystonia and/or LHON is high (see, e.g., Novotny, et al., *Neurology* 36:1053–1060 (1986)). Therefore, family planning is an important utility stemming from the detection of the 14459 mutation. Other concerns can also be addressed in advance by the subject having the mutation and/or the subject's family for planning for the time when the subject will be afflicted by the disease.

Additionally, the discovery of this mutation allows the creation of animal models of dystonia and/or Leber's Hereditary Neuropathy. These animals can be used, for example, to screen drugs for usefulness in treating the clinical manifestations of dystonia and/or LHON.

Other utilities for the present invention, such as exemplified above, will be readily apparent to the skilled artisan.

The present invention is more particularly described in the following examples which are intended as illustrative only since numerous modifications and variations therein will be apparent to those skilled in the art.

EXAMPLES

Pedigree 1

The pedigree numbers, clinical features, and ages of individuals in this study are taken from our original report (Novotny, et al., *Neurology* 36:1053–1060 (1986)).

The sequenced proband (IV-36) was a 10 year old female with onset of mild clinical manifestations at two years progressing to generalized dystonia at five years. By eight years, corticospinal tract dysfunction, dysarthria, and extraocular muscle involvement were observed. CT and MRI examination revealed bilateral, low-density lesions of the putamina at two years which progressed to the caudate nuclei at eight years, with similar bilateral lesions within the regions of the centromedian nuclei.

Patient IV-35 at 13 years had a milder dystonia but greater intellectual impairment. Patient III-10 experienced at 32 years the bilateral optic atrophy of LHON. Individual III-F is the unaffected father of IV-36. Individual III-5 is an obligate carrier and mother of LHON patient IV-26. Patient V-11 presented at five years with mild, generalized dystonia and abnormal basal ganglia lucencies on CT scan.

Tissue Samples and DNA Isolation: Total genomic DNA was extracted from buffy coat (III-10, III-F, IV-26, IV-35, IV-36, and controls), PHA-stimulated lymphocytes (III-5), and platelets (V-11) by standard methods.

Mitochondrial DNA Haplotype and Phylogenetic Analysis: MTDNA haplotypes were determined as described (Torroni, et al., *Am. J. Hum. Genet.* 53:563–590 (1993)). The phylogenetic relationship between the family's mtDNA haplotype and 120 additional Native American mtDNA haplotypes was determined by parsimony analysis (PAUP version 3.0S). The resulting tree included 508 individuals and 131 character states, was 173 steps in length with consistency and retention indices of 0.564 and 0.894, respectively, and was rooted using a Senegalese mtDNA (FIG. 1).

Mitochondrial DNA Sequence Analysis: MTDNA was asymmetrically PCR-amplified and directly sequenced using Amplitaq (Perkin-Elmer/Cetus) or Sequenase (United States Biochemical) protocols. Ambiguities were resolved by sequencing the opposite DNA strand or by diagnostic restriction endonuclease digestion.

Restriction Enzyme Analysis and Population Surveys of mtDNA Variants: Population screens for the np 2092, 3010, 8414, 9966, and 14459 mutations included mtDNAs from 38 clinically normal haplogroup D Native Americans and a large number of unrelated African, Asian, and Caucasian mtDNAs. Haplogroup D mtDNAs were from North (n=7), Central (n=1), and South America (n=30) (28). Caucasian mtDNAs were from North America (n=93) and Italy (n=10). African mtDNAs were from Senegal and included ethnic Mandenka (n=60) and others (n=39) including Wolof and Peuls. Asian mtDNAs were from Taiwan (n=21); Malaysia including ethnic Sabah (n=28) and Malay (n=7); Tibet (n=39); and Korea (n=13).

Tests for known pathogenic mtDNA mutations included LHON (nps 11778, 3460, 4160, 15257, 14484); MERRF (np 8344); MELAS (nps 3243, 3271, 11084); cardiomyopathy plus myopathy (np 3260); mitochondrial myopathy (np 3250); and NARP/Leigh's disease (np 8993). PCR-based restriction enzyme tests for base substitutions at nps 2092, 3010, 8414, 9966, and 14459 were designed using mismatched PCR primers (Brown, M. D., et al., *Genetics* 130:163–173 (1992)). Coordinates of all nucleotide pairs given correspond to the published human mtDNA sequence (Ozawa, et al., *Biochem. Biophys. Res. Commuun.* 177:518–525 (1991)).

For np 2092, the forward primer extended from np 2063 to np 2091 (5' to 3') with a mismatched A at np 2087, creating an AseI (New England Biolabs, NEB) site in the presence of a C to T transition at np 2092. The reverse primer extended from np 2881 to 2900 (3' to 5'). AseI digestion yielded 684 and 153 bp fragments for normal and 658, 153, and 26 bp fragments for mutant mtDNAs.

For np 3010, the forward primer extended from np 2981 to np 3009 (5' to 3') with a mismatched G at np 3008, creating a BstUI (NEB) site in the presence of a G to A transition at np 3010. The reverse primer extended from np 3351 to np 3370 (3' to 5'). BstUI digestion yielded an uncut 389 bp product for normal and 362 and 27 bp fragments in mutant mtDNAs.

For np 8414, the forward primer extended from np 8374 to np 8413 (5' to 3') with a mismatched A at np 8410 creating an SspI (NEB) site in the presence of a C to T transition at np 8414. The reverse primer extended from np 8608 to np 8628 (3' to 5'). SspI digestion yielded 180 and 74 bp fragments for normal and 180, 38, and 36 bp fragments for mutant mtDNAs.

For np 9966, the forward primer extended from np 9802 to np 9821 (5' to 3') and the reverse primer from np 10356 to np 10375 (3' to 5'). BsmAI (NEB) digestion yielded 409 and 164 bp fragments for normal and an uncut 573 bp fragment for mutant mtDNAs. All putative np 9966 G to A mutations identified by this test were verified by sequencing.

For np 14459, the forward primer extended from np 14430 to np 14458 (5' to 3') with a mismatched G at np 14456, creating a Mae III (Boehringer-Mannheim) site in the presence of a G to A transition at np 14459 on the L-strand. The reverse primer extended from np 14855 to np 14874 (3' to 5'). Mae III digestion yielded an uncut 444 bp fragment for normal and 419 and 25 bp fragments for mutant mtDNAs. For Mae III digestions, 1 ml of enzyme was added to 20 ml total reaction volume, incubated at 55° C. for 12 hours with an additional 1 ml of Mae III and incubation for 4 hours at 55° C. Prior to the addition of agarose gel loading dye, samples were heated to 95° C. for 5'.

For the np 14459 mutation, heteroplasmy was quantitated by 1-dimensional densitometry using an Ultroscan XL densitometer equipped with Gel-Scan XL software, version 2.0 (Pharmacia LKB Biotechnology) and type 55 Polaroid negatives of ethidium bromide stained agarose gels.

Haplotype and phylogenetic analysis of Pedigree 1 reveals a Native American mtDNA: MtDNA haplotypes determined for IV-36, III-10 and IV-35 differed from the standard "Cambridge" sequence (Ozawa, et al. (1991)) by twelve restriction site variants. Seven of these variants, an AluI site loss at np 4769, an AluI site gain at np 7025, a HhaI site gain at np 8858, a HaeIII site loss at np 13702, a HincII site loss at np 14199, a HinfI site gain at np 14268, and a HinfI site loss at np 14368, have been previously observed in multiple population studies, indicating that they are very common polymorphisms or "errors" in the published sequence. Four of the site variants, an AluI site loss at np 5176, a DdeI site gain at np 10394, an AluI site gain at np 10397, and a HaeIII site gain at np 16517, are common, non-pathogenic polymorphisms characteristic of certain human populations. Among these, the site variants at nps 5176, 10394, 10397 define haplogroup D, one of four Native American-specific mtDNA haplogroups designated A, B, C and D. Thus, the mtDNA of this Hispanic pedigree is of Native American origin. The twelfth variant, a HaeIII site gain at np 11092, has not been observed in previous population surveys. No mtDNA length polymorphisms were observed on haplotyping, a result confirmed by Southern analysis.

The close relationship of the LHON and dystonia family's mtDNA haplotype with the other 16 haplotypes (38 individuals) of haplogroup D is shown in the maximum parsimony phylogeny of 120 Native American haplotypes (FIG. 1). The proband's mtDNA represents a new branch of the Native American haplogroup D mtDNA lineage, delineated by a novel HaeIII site generated by a silent A to G transition at np 11092.

MtDNA sequence analysis reveals a novel np 14459 variant: The mtDNA genome of IV-36 was sequenced to the following extent: D-loop region (98%), tRNA genes (92%), rRNA genes (80%), and protein coding genes (92%). In addition to the twelve RFLP variants discussed above, 28 base substitutions were identified, giving a total of 40 base substitutions relative to the Cambridge sequence. No known pathogenic mtDNA mutations were observed, a result confirmed by mutation-specific restriction endonuclease digests. The data is summarized below in Table 1.

TABLE 1

MTDNA Sequence Variants in LHON and Dystonia Proband IV-36

| | Gene | Nucleotide Position | Base Change | Amino Acid Change | Nucleotide or Amino Acid Conservation (H/B/M/X) |
|---|---|---|---|---|---|
| 1. | 16S rRNA | 2092 | C to T | — | C/A/A/G |
| 2. | ND2 | 4883 | C to T | synonymous | |
| 3. | COI | 6179 | G to A | synonymous | |
| 4. | COI | 7055 | A to C | synonymous | |
| 5. | ATP8 | 8414 | C to T | L to F | L/F/M/W |
| 6. | COIII | 9966 | G to A | V to I | V/V/V/V |
| 7. | ND3 | 10163 | C to A | synonymous | |
| 8. | ND4L | 10538 | C to T | synonymous | |
| 9. | ND4 | 11092 | A to G | synonmous | |
| 10. | ND5 | 14459 | G to A | A to V | A/A/A/A |
| 11. | | ND6 | 14668 | C to T | synonymous |
| 12. | | CYTB | 14783 | T to C | synonymous |
| 13. | | CYTB | 15043 | G to A | synonymous |
| 14. | | CYTB | 15301 | G to A | synonymous |

Table 1 notes.
Previously reported polymorphisms or Cambridge sequencing errors found in the proband include mutations at nps 263, 489, 750, 3010, 3423, 4769, 4985, 5178, 7028, 8701, 8860, 9540, 10398, 10400, 10873, 11335, 12705, 13702, 14199, 14272, 14365, 14368, 15326, 16223, 16291, 16519 (8, 11, 12, 13, 28, 31, 32, 34, 35, 37, 38, 39, 41, 42, 43, 44, 61). Mutations are reported here as L-strand base changes.

The majority of the 40 variants could be excluded from an etiologic role in this disease. Seventeen variants (nps 3423, 4883, 4985, 6179, 7055, 9540, 10163, 10400, 0538, 10873, 11092, 11335, 12705, 14668, 14783, 15043, and 15301) were silent substitutions within protein-coding genes. Ten variants (nps 263, 4769, 7028, 8860, 13702, 14199, 14272, 14365, 14368, and 15326) have either been observed in all individuals or in certain ethnic groups and thus are either errors in the Cambridge sequence or ethnic-specific variants. Four variants (nps 750, 8701, 10398, and 16519) have been observed at significant polymorphic frequencies in some ethnic groups (8,11,12,28,31,35,37–39). Three variants (nps 489, 16223, and 16291) occur in the non-coding D-loop region and have been observed previously (28,40,42 and M.D.B. and D. C. W. unpublished data). One variant (np 5178) is found in all Native American haplogroup D mtDNAs and defines that group.

The five remaining variants (nps 2092, 3010, 8414, 9966, and 14459) were missense substitutions and were investigated further. Three of these variants (nps 3010, 8414, and 9966) have been observed previously, while two (nps 2092 and 14459) were new. The C to T transition at np 2092 alters a non-conserved nucleotide in the 16S rRNA gene (Table 1). Screening for this variant revealed its presence in 35 of 37 haplogroup D controls. Thus, it is a common Native American haplogroup D polymorphism. The G to A transition at np 3010 changes a moderately conserved nucleotide in the 16S rRNA gene (Table 1). Screening for this variant revealed that 6 of 36 haplogroup D Native Americans had this variant, suggesting a neutral polymorphism. The C to T transition at np 8414 converts a non-conserved leucine to phenylalanine at codon 17 of the ATPase 8 gene (Table 1). All Native American haplogroup D mtDNAs had this variant. Hence, this marker is haplogroup D-specific. The G to A transition at np 9966 substitutes an isoleucine for a valine at codon 254 of the COIII gene. This amino acid is moderately conserved among animal species, although an isoleucine is found at the corresponding position in *Drosophila yakuba*. Population screening revealed that this variant was absent in 37 Native American haplogroup D mtDNAs and 59 random Asians, but it was found in 1/60 (1.7%) African and 2/65 (3.1%) Caucasian control mtDNAs. Hence, this is a rare variant of possible relevance, but it is unlikely to be the primary disease mutation. The G to A transition at np 14459 changes a moderately conserved alanine to valine at codon 72 of the ND6 gene (Table 2). All mammals have an alanine at this position and all reported mtDNAs have either an alanine or serine, with the exceptions of fungus (leucine) and liverwort (phenylalanine), as summarized in Table 2 below.

TABLE 2

Amino Acid Conservation of ND6 Alanine 72

| LHON & DYSTONIA | Y | T | T | V | M | A | I |
|---|---|---|---|---|---|---|---|
| 1. *H. sapiens* | Y | T | T | V | M | A | I |
| 2. *B. bovis* | Y | T | T | A | M | A | T |
| 3. *M. musculus* | Y | T | T | A | M | A | T |
| 4. *R. norvegicus* | Y | T | T | A | M | A | T |
| 5. *B. physalus* | Y | T | T | A | M | A | T |
| 6. *X. laevis* | Y | S | A | A | R | A | K |
| 7. *S. purpuratus* | Y | S | S | A | I | S | — |
| 8. *G. domesticus* | Y | S | V | S | L | A | A |
| 9. *C. japonica* | Y | S | V | S | L | A | A |
| 10. *D. yakuba* | Y | V | T | S | L | A | S |
| 11. *C. elegans* | Y | F | S | S | L | S | K |
| 12. *A. suum* | Y | F | S | S | L | S | K |
| 13. *A. nidulans* | L | T | V | L | L | F | Y |
| 14. *M. polymorpha* | Y | S | N | F | F | V | Y |

Table 2 notes.
Shaded amino acids correspond to codon 72 of the human ND6 polypeptide. References for published amino acid sequences: 1(32); 2(46); 3(47); 4(48); 5(49); 6(50); 7(51); 8(52); 9(53); 10(45); 11 and 12(54); 13(55); 14(56).

A population survey of the np 14459 mutation using mutation-specific primer mismatch PCR and Mae III restriction endonuclease digestion revealed that all 38 Native American haplogroup D mtDNAs analyzed were negative for this mutation. An additional 310 controls including 99 Africans, 108 Asians, and 103 Caucasians were also negative for this mutation, yielding a total of 348 controls tested. Hence, the np 14459 variant is unique to this LHON and dystonia family.

Blood cell mtDNAs of five additional maternal relatives (III-5, III-10, IV-26, IV-35, and V-11) plus the proband's father (III-F) were tested for the np 14459 mutation. The father was negative for the mutation, while all maternal relatives were positive. The buffy coat mtDNA of the proband's mother was heteroplasmic for this mutation, with 78% of her mtDNAs being mutant and 22% being normal. The remaining five maternal relatives were essentially homoplasmic with >99% mutant mtDNAs as determined by laser densitometry.

Analysis of the mtDNA of a patient with juvenile onset dystonia and bilateral striatal necrosis from a family with maternally inherited LHON and dystonia revealed that a heteroplasmic ND6 mutation at np 14459 is the probable cause of this disease. This G to A transition changes a moderately conserved alanine to a valine at codon 72 of the ND6 gene, an amino acid in the "span C" region of ND6, the most evolutionarily conserved sequence of this polypeptide. Interestingly, the known LHON mutation at np 14484 also changes a span C amino acid only eight residues away from the alanine altered by the np 14459 mutation. Like the np 14459 mutation, the np 14484 mutation changes a moderately conserved amino acid and has been observed in a five generation, 136 member Australian family exhibiting maternally inherited LHON, a generalized movement disorder, and infantile encephalopathy. Thus, mutations in this region of ND6 may contribute to neurological disease.

The np 14459 mutation was not found in any of 348 normal controls representing diverse haplotypes from four major racial/ethnic groups: African, Caucasian, Asian, and Native American. The latter group is of particular importance since the patient's mtDNA genotype belongs to Native American haplogroup D, yet none of the 38 individuals in this control group harbor this mutation. Thus the np 14459 mutation is not a rare, ethnic-specific variant, but instead occurred recently in this mtDNA lineage.

The recent occurrence of the np 14459 mutation is further substantiated by the discovery that the mother of the proband is heteroplasmic for the mutation. This implies that this mutation arose in the family concurrently with the appearance of LHON in generation I of this pedigree. Since many of the individuals in the most recent generations have the more severe pediatric dystonia and are essentially homoplasmic for the mutation, it is tempting to speculate that replicative segregation to homoplasmic mutant mtDNAs in affected tissues accounts for the increasing severity of the disease in more recent generations. Thus, the np 14459 mutation fulfills the criteria that would be expected for a mtDNA mutation causing maternally transmitted LHON and dystonia.

Pedigrees 2 and 3

Pedigree 2. A 42 year old African-American female experienced gradual painless loss of vision over several months. Symptoms began in the left eye and became bilateral within one month of onset. Her medical history was negative except for a one pack/day history of cigarette smoking for 15 years and a 2 beer/day history of alcohol use. Her daughter was 19 years old when she experienced her first symptoms. Similar to her mother, she experienced gradual painless loss of vision in both eyes over three months. Her only other symptom was a severe, throbbing, frontal headache without nausea or vomiting that lasted approximately 24 hours. This occurred as an isolated event shortly after the onset of visual loss. Her medical history was negative and no alcohol or tobacco use was identified. Pedigree analysis revealed that the mother and her daughter were the only affected individuals in their family. Except for the ophthalmologic manifestations, neurologic exam in the mother and the daughter were normal. The daughter had no clinical evidence of extrapyramidal dysfunction that would suggest basal ganglia degeneration. The ophthalmologic examinations for the mother and daughter are summarized in Table 3 below.

TABLE 3

Ophthalmologic features of the MTND6*LDYT14459A mutation in the members of pedigree 2 at initial presentation.

| Pedigree 2 | (Mother) 42 year old | Daughter (19 year old) |
|---|---|---|
| Acuity | 20/400 (OD); Count fingers at 6 feet (OS) | Count fingers at 6 feet (OU) |
| Visual Fields | Cecocentral scotoma (OU) | Cecocentral scotoma (OU) |
| Pupils | 5 mm to 3.5 mm (OU; No RAPD | 4.5. mm to 3.5 mm (OU); No RAPD |
| Ocular Motility | Normal | Normal |
| Optic Discs | Temporal pallor (OU) | Temporal pallor (OU) |
| Nerve Fiber | Absent in temporal sector; | Absent in temporal sector; |

TABLE 3-continued

Ophthalmologic features of the MTND6*LDYT14459A mutation in the members of pedigree 2 at initial presentation.

| Pedigree 2 | (Mother) 42 year old | Daughter (19 year old) |
|---|---|---|
| Layer | coarsened and opacified in the arcuate zones | coarsened and opacified in the arcuate zones |
| Retinal Vessels | Peripapillary Telangiectasias (OU) at presentation | Normal except for sheathing of a single peripheral arteriole (OD) |

Table 3 notes.
RAPD, relative afferent pupillary defect. OU, both eyes. OS, left eye. OD, right eye.

The retinal exam from both the mother and her daughter displayed optic atrophy and regional abnormalities in the nerve fiber layer. Shortly after the mother experienced visual loss, peripapillary telangiectasias, a frequently encountered manifestation of LHON, were observed in both eyes of the mother. An examination performed three months later demonstrated that the peripapillary telangiectasias had disappeared in conjunction with further degeneration of the nerve fiber layer. Hence, this 42 year old female is the first person with the MTND6*LDYT14459A mutation observed to have this abnormality during the course of her disease. Peripapillary telangiectasias were absent in the daughter's eyes and in the Hispanic family. No improvements in visual function have been noted in either individual since the onset of symptoms.

Brain MRI in the daughter revealed a unilateral lesion involving the right putamen and bilateral lesions in the caudate nucleus. Complete cell count plus differential, serum electrolytes and routine chemistries, free T4, TSH, creatine kinase, sedimentation rate, rapid plasma reagin test, vitamin $B_{12}$, RBC folate, creatinine clearance, and blood lipid studies which included cholesterol, triglycerides, high density lipoproteins, low density lipoproteins, and very low density lipoproteins were normal. ECG, EEG, and echocardiogram were normal. CSF analysis which included protein, glucose, cell count, VDRL, IgG index, and immunoglobulin electrophoresis for oligoclonal bands was normal. An investigation for metabolic abnormalities indicative of an OXPHOS disease was performed in blood, CSF, and a 24 hour urine collection. Blood, urine, and CSF organic acid analysis was normal. Quantitative amino acids and carnitine levels were normal in blood and urine. The CSF alanine was increased at 47.5 micromoles/liter which is slightly above the upper limits of normal of the referral laboratory (11.5–41.2 micromoles/liter).

Pedigree 3. The proband was a 13 year old Caucasian female who had generalized dystonia and athetosis. No identifiable manifestations of an OXPHOS disease were present along the maternal lineage of this family. Motor and cognitive development were normal until 34 months of age. At that time, she developed dysarthria, mild paresis of her right leg, and mild dystonic posturing of her right arm. A brain CT performed at 37 months of age showed a bilateral decrease in signal intensity in her putamina. At various times during her evaluation, blood lactate levels showed sporadic elevations and pyruvate levels remained normal. Based on her clinical course, radiological findings, and intermittent lactate elevations, she was diagnosed as having Leigh's disease. Her disease manifestations continued to progress with advancing age. By 8 years of age, her head MRI demonstrated extensive basal ganglia involvement with bilateral globus pallidus, putamen, and caudate lesions.

Her examination at 13 years of age revealed severe dystonia, marked dysarthria, quadriparesis, mild thoracic scoliosis, and pes cavus. Sensory exam was normal. In contrast to the large pedigree with LHON plus dystonia in which mental retardation often accompanied the dystonia, this patient had a normal IQ. Metabolic testing revealed no clear abnormality. Quantitative urine organic and amino acids were normal, as was the lactate response to a 1.75 gm/kg glucose load and a 400 mg/kg alanine load. Other investigations which were normal included fasting blood sugar, blood ammonia, serum copper, ceruloplasmin, the blood glucose response to glucagon, and fructose loading.

Therapeutic interventions were unsuccessful. Trials of L-Dopa/carbidopa, tetrabenzine, and baclofen increased her rigidity. The combined use of thiamine, biotin, niacin, vitamin B6, riboflavin, vitamin B12, and L-carnitine had no significant clinical effect.

Genetic and Biochemical Analyses

All mtDNA mutation designations follow Human Gene Map convention and represent L-strand nucleotide changes. Total genomic DNA isolation; testing for the MTND6*LDYT14459A, MTND4*LHON11,778A, MTATP6*NARP8993G, MTI'K*MERRF8344G, MTND1*LHON3460A, MTI'L1*MELAS3271C, and MTTL1*MELAS3243G mutations; and mtDNA Southern blot analysis using BamHI and EcoRV restriction endonucleases was performed as described. The restriction endonuclease, HpaII, was used to detect both the MTATP6*NARP8993G and MTATP6*NARP8993C mutations. The African-American family was screened by restriction endonuclease analysis for the position 5178 (AluI), position 11092 (HaeIII and position 3592 (HpaI) polymorphisms that were observed in the Hispanic family with LHON and dystonia as described.

Analyses for additional mtDNA mutations were performed using the following oligonucleotide primer pairs (forward=→and reverse=←) and restriction endonucleases: (a) MTCYB*LHON15257A mutation: positions 15234–15256 (→) and 15343–15360 (←), T was substituted at position 15254 within the forward primer to create a MseI site when the mutation is present; (b) MTND6*LHON14484C mutation: positions 14191–14210 (→) and 14485–14509 (←), two C's were substituted at positions 14487 and 14488 within the reverse primer to create a MvaI site when the mutation is present; (c) MTTL1*MMC3260G mutation: positions 3242–3259 (→) and 3701–3717 (←), G was substituted at position 3257 within the forward primer to create a DdeI site when the mutation is present; (d) MTTL1*MM3250C mutation: positions 3225–3249 (→) and 3404–3423 (←), G was substituted at position 3245 within the forward primer to create a NaeI site when the mutation is present. Since these mutations do not create naturally occurring restriction sites, the primers were designed to contain a novel nucleotide or nucleotides that are incorporated into the sequence during amplification and generate a restriction site when the mutation is present. DNA electrophoresis was performed with either 8% polyacrylamide or 2.5% NuSieve/0.8% SeaKem agarose gels. The gels were stained with ethidium bromide and mtDNA fragment fluorescence was visualized and quantitated using the Eagle Eye II detection system (Stratagene) with the ImageQuant software package (Molecular Dynamics).

A muscle biopsy was performed on the 19 year old from pedigree 2 and on the pedigree 3 proband. Histochemistry was normal in skeletal muscle from both individuals. Electron microscopy on muscle from the pedigree 3 proband exhibited some mild accumulations of subsarcolemmal mitochondria. Although most of the mitochondria were ultrastructurally normal, some had electron dense inclusions and abnormal cristae.

The specific activities of OXPHOS complexes I–IV were determined for the muscle mitochondria of the 19 year old from pedigree 2. Mitochondria were isolated immediately after the muscle biopsy to minimize the possibility of artifactual reductions in OXPHOS enzyme activities that can be produced during freezing of the muscle sample. A severe reduction in the specific activity of the Complex I assay was observed in this patient, as shown in Table 4. The specific activities of Complex IV and the linked enzyme assays were normal, though the Complex III activity was also slightly below the 5% tolerance level.

TABLE 4

OXPHOS enzyme activity in skeletal muscle mitochondria from a patient with the MTND6*LDYT14459A mutation

| Assay | | 19 year old (Pedigree 2) | Mean ± SD (5% Level) < 50 yrs. |
|---|---|---|---|
| Complex I | NADH-DB | 4 | 144 ± 45 (64) |
| Complex I + III | NADH-Cyt c | 152 | 301 ± 98 (129) |
| Complex II + III | Succinate-Cyt c | 682 | 568 ± 141 (306) |
| Complex III | DBH$_2$-Cyt c | 258 | 1554 ± 387 (838) |
| Complex IV (FT) | Cytochrome c oxidase (FT) | 1209 | 1371 ± 381 (676) |
| Complex IV (SON) | Cytochrome c oxidase (SON) | 1261 | 1857 ± 366 (1157) |

TABLE 4 notes.
Shaded values are below the 5% tolerance limit for normal adults. NADH-DB = NADH-n-decyl coenzyme Q oxidoreductase; NADH-Cyt c = NADH cytochrome c oxidoreductase (rotenone sensitive fraction); succinate-Cyt c = succinate-cytochrome c oxidoreductase; DBH$_2$-Cyt c = reduced n-decyl coenzyme Q-cytochrome c oxidoreductase; FT = freeze thaw disruption of mitochondria; SON = disruption of mitochondria with 6 seconds of sonication. Enzyme activity is reported in nanomoles of substrate/minute/mg mitochondria protein.

Genetic testing for the MTND6*LDYT14459A mutation in pedigrees 2 and 3 was performed on a ND6 fragment which was amplified from leukocyte and/or skeletal muscle mtDNA. The 42 year old female from pedigree 1 was heteroplasmic (50% normal and 50% mutant) in leukocyte mtDNA for the MTND6*LDYT14459A mutation. Mutation analysis in the daughter indicated that the MTND6*LDYT14459A mutation had segregated to homoplasmy in her leukocytes and skeletal muscle. The proband of pedigree 2 was also heteroplasmic for the MTND6*LDYT14459A mutation, with approximately 50% mutant and 50% normal mtDNA. The MTTK*MERRF8344G, MTATP6*NARP8993G, MTATP6*NARP8993C, MTTL1*MELAS3271C, MTTL1*MMC3260G, MTTL1*MM3250C, and MTTLI*MELAS3243G mutations were not present in these individuals' mtDNA. This identification of the MTND6*LDYT14459A mutation in two additional pedigrees, one with LHON and basal ganglia lesions and another with dystonia and basal ganglia lesions, confirms the previously reported association of this mutation with these disease manifestations.

The Hispanic family that was originally reported to harbor the MTND6*LDYT14459A mutation (pedigree 1) was previously classified by mtDNA haplotype analysis as belonging to one of four Native American Indian mtDNA lineages referred to as haplogroup D. In order to assess whether the MTND6*LDYT14459A mutation in the African-American family had occurred independently on this mtDNA lineage, pedigree 2 mtDNA was screened for polymorphisms that would distinguish between the two mtDNA lineages. The mtDNAs from the Hispanic and African-American families differed at all three sites tested: (a) the Native American Indian haplogroup D specific variant at position 5178 that was present in the Hispanic family; (b) the position 11092 variant that was unique to the Hispanic family; and (c) the position 3592 variant identified in pedigree 1 that is specific for African derived mtDNA lineages. Hence, these results confirmed that the MTND6*LDYT14459A mutation occurred independently in these two mtDNA lineages.

Other Analyses

To assess the overall clinical importance of the MTND6*LDYT14459A mutation, three groups of patients (LHON, dystonia and Leigh's Syndrome) were screened for this mutation. Twenty-eight LHON patients were tested for the MTND6*LDYT14459A mutation. Of these, 12 individuals (7 males and 5 females, age range 18 to 68) manifested LHON alone, two individuals had LHON and deafness, one had LHON and Charcot-Marie-Toothe disease, one had LHON and cardiomyopathy, one had LHON and complex neurodegeneration, and 11 were referred as possible LHON. None of these individuals harbored the four primary LHON-mutations [MTND4*LHON11778A, MTND1*LHON3460A, MTND6*LHON14484C, and MTCYB*LHON15257A] which account for at least 90% of LHON cases (11). One of the 12 individuals with LHON harbored two secondary mtDNA variants frequently associated with LHON, the MTNDI*LHON4216C and MTND2*LHON4917G mutations. None of these 28 LHON patients had the MTND6*LDYT14459A mutation. Hence, this mutation is not a common cause of LHON. Since basal ganglia lesions are an unusual finding in LHON, their presence might provide an important criterion for identifying LHON patients with this mutation.

Eight patients with dystonia as a prominent neurological manifestation (age range 2.5 to 53 years) were tested for the MTND6*LDYT14459A mutation. Two individuals had pure dystonias whereas the other seven individuals had dystonias that were associated with complex neurological manifestations including ataxia, myoclonic epilepsy, deafness, dementia, pigmentary retinal degeneration, and ophthalmoparesis. Tests were performed on skeletal muscle DNA from six patients and leukocyte and platelet DNAs from two individuals. Tests for other mtDNA mutations commonly associated with generative disease were all negative. These included MTATP6*NARP8993G, MTATP6*NARP8993C, and MTTL1*MELAS3243G for seven of the patients, MTTK*MERRF8344G and MTTL1*MELAS3271C for five of the patients, MTTK*MERRF8356C and MTND4*LHON I1778A for two patients and MTND1*LHON3460A and MTND6*LHON14484C for one patient. Rearrangements of mtDNA were ruled out by analysis of Southern blots of BamHI and EcoRV restriction fragments for six of the patients. All eight patients proved to be negative for the MTND6*LDYT14459A mutation.

Finally, 19 patients (age range 6 months to 14 years) with clinical and neuroimaging features of Leigh's Syndrome were tested for the MTND6*LDYT14459A mutation. Tests were performed on skeletal muscle DNA for 15 patients and on leukocyte and platelet DNA for four patients. None of these patients harbored the MTATP6*NARP8993G or MTATP6*NARP8993C mutations, and none of the individuals tested had other known pathological mtDNA mutations. The additional mutations tested included MTTL1*MELAS3243G in 18 patients, MTTK*MERRF8344G in 15 patients, MTTL1*MELAS3271C in 10 patients, MTND1*LHON3460A and MTND6*LHON14484C in one patient, and mtDNA rearrangements as tested in BamHI and EcoRV Southern blots in 15 patients. All 19 of these Leigh's patients were also negative for the MTND6*LDYT14459A mutation. Hence, this mutation is not a prevalent cause of Leigh's disease.

The analyses of these three pedigrees revealed several important features of the MTND6*LDYT14459A mutation. First, the MTND6*LDYT14459A mutation can be associated with a significant abnormality in Complex I specific activity, consistent with its proposed effect on the ND6 subunit of this enzyme. In the one individual who was homoplasmic for the MTND6*LDYT14459A mutation, the specific activity of this enzyme in the Complex I assay was virtually abolished in skeletal muscle mitochondria.

Second, heteroplasmy or homoplasmy for this mutation in skeletal muscle and leukocyte mtDNA is not a direct predictor of either the LHON or dystonia phenotype. In mtDNA fragments that were amplified from lymphoblast mtDNA of the Hispanic family, five individuals with dystonia were homoplasmic for this mutation and one individual with LHON was heteroplasmic. In contrast, the MTND6*LDYT14459A mutation was homoplasmic in leukocyte and skeletal muscle mtDNA in the 19 year old individual with LHON and asymptomatic basal ganglia lesions, whereas the mutation was heteroplasmic in the leukocyte mtDNA from the 42 year old individual with LHON from pedigree 1 and in the skeletal muscle mtDNA from the pedigree 2 proband with generalized dystonia, basal ganglia degeneration, and no evidence of LHON.

Third, phenotypic manifestations of the MTND6*LDYT14459A mutation are expressed in both sexes with roughly equal probability. In the large Hispanic pedigree (2), LHON occurred in 4 males and 3 females (male:female ratio=1.3) and dystonia occurred in 6 males and 8 females (male:female ratio=0.75). The affected individuals in pedigrees 1 and 2 were both females. This differs markedly from other LHON mutations which show a strong male bias in expression. For example, 80% of the affected individuals of European descent who harbor the MTND4*LHON11778A mutation are males.

Fourth, the MTND6*LDYT14459A mutation can result in either large pedigrees with multiple affected relatives or in singleton cases (pedigree 2). This broad variability in the penetrance of clinical manifestations is frequently encountered in families that harbor mtDNA mutations. In fact, large pedigrees that clearly delineate maternal transmission of an OXPHOS disease are unusual. Therefore, patient phenotype is often more useful for determining whether an OXPHOS disease evaluation is warranted than the presence or absence of maternal inheritance.

Inheritance of the MTND6*LDYT14459A mutation can cause LHON or dystonia. It is possible that an important parameter that determines disease penetrance is the concentration of the mutant mtDNA within the optic pathway and basal ganglia. Other important variables could include nuclear-cytoplasmic interactions and environmental insults.

To define the prevalence of the MTND6*LDYT14459A mutation and the spectrum of clinical manifestations associated with it, LHON, dystonia and Leigh's syndrome cases which had not been attributed to other known pathogenic mutations were surveyed. The prevalence of the MTND6*LDYT14459A mutation in atypical LHON was one out of 29 pedigrees or about 3%, 1 out of 9 cases with dystonia or 10%, and zero out of 20 cases with Leigh's disease or less than 1%.

The breadth of clinical manifestations caused by the MTND6*LDYT14459A mutation was observed. The symptoms were confined to LHON and dystonia in the three pedigrees and the dystonia patients were generally children and frequently exhibited unilateral or bilateral basal ganglia lesions. Among the pediatric dystonia patients harboring the MTND6*LDYT14459A mutation, the clinical manifestations ranged from a pure dystonia with normal cognition (pedigree 2 proband) to more complex neurological degeneration that included dystonia, pseudobulbar signs, corticospinal tract dysfunction, and mental retardation (Novotny, et al. (1986)).

Interestingly, while the expected muscle mitochondrial Complex I defect was observed in the one patient tested, the MTND6*LDYT14459A mutation is not associated with other traditional indicators of OXPHOS disease. Patients with this mutation rarely show elevated blood or urine lactate, pyruvate, or alanine. Moreover, they do not exhibit the "ragged-red muscle fiber (RRF)" pathology that is observed in certain classes of OXPHOS diseases. RRFs are associated with the accumulation of subsarcolemmal aggregates of mitochondria which stain red with Gomori-Trichrome staining. Ultrastructural analysis of RRFs of ten reveals mitochondria with abnormalities in the membrane structure and paracrystalline inclusions which are caused by increased expression and aggregation of the mitochondrial isoform of creatine kinase. RRFs have frequently been associated with mtDNA mutations which inhibit protein synthesis such as mtDNA deletions that cause chronic progressive ophthalmoplegia syndromes and tRNA mutations that cause diseases like MERRF and MELAS. They have not been observed in association with pathologic missense mutations in the electron transport chain that cause LHON or mutations in the mtDNA ATPase 6 gene [MTATP6*NARP8993G, MTATP6*NARP8993C] causing Leigh's syndrome. Hence, the MTND6*LDYT14459A provides further support of the concept that RRFs are primarily seen in OXPHOS diseases caused by defects in mitochondrial protein synthesis.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of detecting in a subject the presence of a class of dystonia and/or Leber's Hereditary Optic Neuropathy, comprising detecting in a sample from the subject the presence of a mutation at position 14459 of mitochondrial DNA, the presence of the mutation indicating the presence of the class of dystonia and/or Leber's Hereditary Optic Neuropathy in the subject.

2. The method of claim 1, wherein the detecting step comprises amplifying a region of the mitochondrial DNA including nucleotide 14459 and detecting the presence of the mutation at position 14459 in the amplified product, the presence of the mutation in the amplified product indicating the presence of the class of dystonia and/or Leber's Hereditary Optic Neuropathy.

3. The method of claim 1, wherein the detecting step comprises selectively amplifying mitochondrial DNA having the mutation at position 14459 and detecting the presence of amplification, the presence of amplification indicating the presence of the class of dystonia and/or Leber's Hereditary Optic Neuropathy.

4. The method of claim 3, wherein the amplification comprises a ligase chain reaction.

5. A method of predicting a predisposition to developing symptoms of a class of dystonia and/or Leber's Hereditary Optic Neuropathy, comprising detecting in a sample from a subject the presence of a mutation at position 14459 of mitochondrial DNA, the presence of the mutation indicating a predisposition to developing symptoms of the class of dystonia and/or Leber's Hereditary Optic Neuropathy in the subject.

* * * * *